United States Patent
Shalev (10) Patent No.: US 8,979,892 B2
(45) Date of Patent: Mar. 17, 2015

(54) APPARATUS FOR CLOSURE OF A LUMEN AND METHODS OF USING THE SAME

(75) Inventor: Alon Shalev, Ra'anana (IL)

(73) Assignee: Endospan Ltd., Netanya (IL)

( * ) Notice: Subject to any disclaimer, the term of this patent is extended or adjusted under 35 U.S.C. 154(b) by 694 days.

(21) Appl. No.: 13/383,128

(22) PCT Filed: Jul. 8, 2010

(86) PCT No.: PCT/IL2010/000549
§ 371 (c)(1),
(2), (4) Date: Mar. 22, 2012

(87) PCT Pub. No.: WO2011/004374
PCT Pub. Date: Jan. 13, 2011

(65) Prior Publication Data
US 2012/0172929 A1 Jul. 5, 2012

Related U.S. Application Data

(60) Provisional application No. 61/224,089, filed on Jul. 9, 2009.

(51) Int. Cl.
A61B 17/03 (2006.01)
A61F 2/90 (2013.01)
(Continued)

(52) U.S. Cl.
CPC ... *A61F 2/90* (2013.01); *A61F 2/07* (2013.01); *A61F 2/844* (2013.01); *A61F 2/95* (2013.01);
(Continued)

(58) Field of Classification Search
CPC ..... A61F 2/844; A61F 2/07; A61F 2002/072; A61F 2/02; A61F 2/04; A61F 2/06
USPC ................ 606/213; 623/1.16, 1.11, 1.1, 1.15, 623/1.18, 1.23, 1.44, 1.49
See application file for complete search history.

(56) References Cited

U.S. PATENT DOCUMENTS 4,355,426 A 10/1982 MacGregor
4,505,767 A 3/1985 Quin
(Continued)

FOREIGN PATENT DOCUMENTS

CA 2 497 704 3/2004
CN 2817770 Y 9/2006
(Continued)

OTHER PUBLICATIONS

"E-vita® open plus" product brochure (JOTEC GmbH, Hechingen, Germany), 2010.
(Continued)

*Primary Examiner* — Julian W Woo
*Assistant Examiner* — Shaun L David
(74) *Attorney, Agent, or Firm* — Sughrue Mion, PLLC (57) ABSTRACT

A generally tubular endovascular prosthesis (100) is configured to transition between a radially-compressed state and a radially-expanded state. The prosthesis (100) includes a first generally cylindrical structural portion (101), which has first and second ends (102, 103), and a second generally cylindrical structural portion (104), which has first and second ends (105, 106). The first end (102) of the first structural portion (101) and the first end (105) of the second structural portion (104) meet each other at a juncture (107). The prosthesis (100) is configured to transition from (a) an initial folded state, in which the second structural portion (104) is folded into the first structural portion (101) at the juncture (107), to (b) an unfolded state, in which the second structural portion (104) is no longer positioned within the first structural portion (101), and the second end (103) of the first structural portion (101) and the second end (106) of the second structural portion (104) are positioned at opposite ends of the prosthesis (100). Other embodiments are also described.

31 Claims, 7 Drawing Sheets

(51) Int. Cl.
  *A61F 2/07* (2013.01)
  *A61F 2/844* (2013.01)
  *A61F 2/95* (2013.01)
  *A61F 2/06* (2013.01)
  *A61F 2/30* (2006.01)

(52) U.S. Cl.
  CPC . *A61F 2002/068* (2013.01); *A61F 2002/30329* (2013.01); *A61F 2002/9505* (2013.01); *A61F 2220/0025* (2013.01); *A61F 2250/0039* (2013.01); *A61F 2230/0078* (2013.01)
  USPC .......................................... 606/213; 623/1.16

(56) References Cited

U.S. PATENT DOCUMENTS

| | | |
|---|---|---|
| 4,562,596 A | 1/1986 | Kornberg |
| 4,577,631 A | 3/1986 | Kreamer |
| 4,617,932 A | 10/1986 | Kornberg |
| 4,665,906 A | 5/1987 | Jervis |
| 4,739,762 A | 4/1988 | Palmaz |
| 4,787,899 A | 11/1988 | Lazarus |
| 4,878,906 A | 11/1989 | Lindemann et al. |
| 4,886,062 A | 12/1989 | Wiktor |
| 4,938,740 A | 7/1990 | Melbin |
| 4,969,458 A | 11/1990 | Wiktor |
| 5,042,707 A | 8/1991 | Taheri |
| 5,064,435 A | 11/1991 | Porter |
| 5,104,404 A | 4/1992 | Wolff |
| 5,122,136 A | 6/1992 | Guglielmi et al. |
| 5,133,732 A | 7/1992 | Wiktor |
| 5,234,448 A | 8/1993 | Wholey et al. |
| 5,383,926 A | 1/1995 | Lock |
| 5,456,694 A | 10/1995 | Marin et al. |
| 5,486,183 A | 1/1996 | Middleman et al. |
| 5,507,769 A | 4/1996 | Marin et al. |
| 5,509,923 A | 4/1996 | Middleman et al. |
| 5,522,880 A | 6/1996 | Barone et al. |
| 5,527,322 A | 6/1996 | Klein et al. |
| 5,549,662 A | 8/1996 | Fordenbacher |
| 5,554,181 A | 9/1996 | Das |
| 5,556,413 A | 9/1996 | Lam |
| 5,562,724 A | 10/1996 | Vorwerk et al. |
| 5,607,445 A | 3/1997 | Summers |
| 5,613,974 A | 3/1997 | Andreas et al. |
| 5,632,746 A | 5/1997 | Middleman et al. |
| 5,632,763 A | 5/1997 | Glastra |
| 5,632,772 A | 5/1997 | Alcime et al. |
| 5,639,278 A | 6/1997 | Dereume et al. |
| 5,643,340 A | 7/1997 | Nunokawa |
| 5,653,743 A | 8/1997 | Martin |
| 5,676,696 A | 10/1997 | Marcade |
| 5,676,697 A | 10/1997 | McDonald |
| 5,728,134 A | 3/1998 | Barak |
| 5,749,879 A | 5/1998 | Middleman et al. |
| 5,755,770 A | 5/1998 | Ravenscroft |
| 5,755,771 A | 5/1998 | Penn et al. |
| 5,755,777 A | 5/1998 | Chuter |
| 5,755,781 A | 5/1998 | Jayaraman |
| 5,769,882 A | 6/1998 | Fogarty et al. |
| 5,769,884 A | 6/1998 | Solovay |
| 5,782,903 A | 7/1998 | Wiktor |
| 5,782,906 A | 7/1998 | Marshall et al. |
| 5,824,040 A | 10/1998 | Cox et al. |
| 5,827,321 A | 10/1998 | Roubin |
| 5,855,600 A | 1/1999 | Alt |
| 5,860,991 A | 1/1999 | Klein et al. |
| 5,876,432 A | 3/1999 | Lau et al. |
| 5,906,641 A | 5/1999 | Thompson et al. |
| 5,921,994 A | 7/1999 | Andreas et al. |
| 5,980,552 A | 11/1999 | Pinchasik |
| 6,015,431 A | 1/2000 | Thornton et al. |
| 6,016,810 A | 1/2000 | Ravenscroft |
| 6,033,435 A | 3/2000 | Penn et al. |
| 6,036,725 A | 3/2000 | Avellanet |
| 6,049,824 A | 4/2000 | Taheri |
| 6,099,497 A | 8/2000 | Adams et al. |
| 6,117,145 A | 9/2000 | Wood et al. |
| 6,156,064 A | 12/2000 | Chouinard |
| 6,176,875 B1 | 1/2001 | Lenker et al. |
| 6,179,878 B1 | 1/2001 | Duerig et al. |
| 6,200,339 B1 | 3/2001 | Leschinsky et al. |
| 6,206,893 B1 | 3/2001 | Klein et al. |
| 6,270,524 B1 | 8/2001 | Kim |
| 6,283,991 B1 | 9/2001 | Cox et al. |
| 6,287,335 B1 * | 9/2001 | Drasler et al. ............... 623/1.28 |
| 6,290,720 B1 | 9/2001 | Khosravi et al. |
| 6,296,661 B1 | 10/2001 | Davila et al. |
| 6,312,458 B1 | 11/2001 | Golds |
| 6,325,823 B1 | 12/2001 | Horzewski et al. |
| 6,344,056 B1 | 2/2002 | Dehdashtian |
| 6,428,565 B1 | 8/2002 | Wisselink |
| 6,451,051 B2 | 9/2002 | Drasler et al. |
| 6,471,722 B1 | 10/2002 | Inoue |
| 6,506,211 B1 | 1/2003 | Skubitz et al. |
| 6,613,078 B1 | 9/2003 | Barone |
| 6,635,083 B1 | 10/2003 | Cheng et al. |
| 6,652,567 B1 | 11/2003 | Deaton |
| 6,656,214 B1 | 12/2003 | Fogarty et al. |
| 6,692,520 B1 | 2/2004 | Gambale et al. |
| 6,695,833 B1 | 2/2004 | Frantzen |
| 6,699,277 B1 * | 3/2004 | Freidberg et al. ............ 623/1.13 |
| 6,716,238 B2 | 4/2004 | Elliott |
| 6,743,195 B2 | 6/2004 | Zucker |
| 6,752,826 B2 | 6/2004 | Holloway et al. |
| 6,776,794 B1 | 8/2004 | Hong et al. |
| 6,814,747 B2 | 11/2004 | Anson et al. |
| 6,814,749 B2 | 11/2004 | Cox et al. |
| 6,814,752 B1 | 11/2004 | Chuter |
| 6,824,560 B2 | 11/2004 | Pelton |
| 6,846,321 B2 | 1/2005 | Zucker |
| 6,907,285 B2 | 6/2005 | Denker et al. |
| 6,908,477 B2 | 6/2005 | McGuckin, Jr. et al. |
| 6,929,660 B1 | 8/2005 | Ainsworth et al. |
| 6,942,691 B1 | 9/2005 | Chuter |
| 6,964,679 B1 | 11/2005 | Marcade et al. |
| 6,986,774 B2 | 1/2006 | Middleman et al. |
| 7,008,441 B2 | 3/2006 | Zucker |
| 7,044,962 B2 | 5/2006 | Elliott |
| 7,105,020 B2 | 9/2006 | Greenberg et al. |
| 7,112,217 B1 | 9/2006 | Kugler et al. |
| 7,115,127 B2 | 10/2006 | Lindenbaum et al. |
| 7,144,421 B2 | 12/2006 | Carpenter et al. |
| 7,201,772 B2 | 4/2007 | Schwammenthal et al. |
| 7,223,266 B2 | 5/2007 | Lindenbaum et al. |
| 7,270,675 B2 | 9/2007 | Chun et al. |
| 7,279,003 B2 | 10/2007 | Berra et al. |
| 7,294,147 B2 | 11/2007 | Hartley |
| 7,306,623 B2 | 12/2007 | Watson |
| 7,341,598 B2 | 3/2008 | Davidson et al. |
| 7,407,509 B2 | 8/2008 | Greenberg et al. |
| 7,429,269 B2 | 9/2008 | Schwammenthal et al. |
| 7,442,204 B2 | 10/2008 | Schwammenthal et al. |
| 7,473,272 B2 | 1/2009 | Pryor |
| 7,537,609 B2 | 5/2009 | Davidson et al. |
| 7,540,881 B2 | 6/2009 | Meyer et al. |
| 7,544,160 B2 | 6/2009 | Gross |
| 7,637,939 B2 | 12/2009 | Tischler |
| 7,662,161 B2 | 2/2010 | Briganti et al. |
| 7,662,168 B2 | 2/2010 | McGuckin, Jr. et al. |
| 7,678,141 B2 | 3/2010 | Greenan et al. |
| 7,722,626 B2 | 5/2010 | Middleman et al. |
| 7,731,732 B2 | 6/2010 | Ken |
| 7,803,178 B2 | 9/2010 | Whirley et al. |
| 7,815,673 B2 | 10/2010 | Bloom et al. |
| 7,887,575 B2 | 2/2011 | Kujawski |
| 7,959,662 B2 | 6/2011 | Erbel et al. |
| 8,021,418 B2 | 9/2011 | Gerberding et al. |
| 8,066,755 B2 | 11/2011 | Zacharias et al. |
| 8,080,053 B2 | 12/2011 | Satasiya et al. |
| 8,172,892 B2 | 5/2012 | Chuter et al. |
| 8,257,423 B2 | 9/2012 | Kerr |
| 8,292,951 B2 | 10/2012 | Muzslay |
| 2001/0000188 A1 | 4/2001 | Lenker et al. |

(56) References Cited

U.S. PATENT DOCUMENTS

| | | |
|---|---|---|
| 2001/0004705 A1 | 6/2001 | Killion |
| 2001/0014823 A1 | 8/2001 | Resseman et al. |
| 2001/0044651 A1 | 11/2001 | Steinke et al. |
| 2001/0044652 A1 | 11/2001 | Moore |
| 2001/0047198 A1 | 11/2001 | Drasler et al. |
| 2001/0049550 A1 | 12/2001 | Martin et al. |
| 2001/0053930 A1 | 12/2001 | Kugler et al. |
| 2002/0040236 A1 | 4/2002 | Lau et al. |
| 2002/0099441 A1 | 7/2002 | Dehdashtian |
| 2002/0107564 A1 | 8/2002 | Cox |
| 2002/0111667 A1 | 8/2002 | Girton |
| 2002/0123791 A1 | 9/2002 | Harrison |
| 2002/0156495 A1 | 10/2002 | Brenneman et al. |
| 2002/0173809 A1 | 11/2002 | Fleischman et al. |
| 2002/0193864 A1 | 12/2002 | Khosravi et al. |
| 2003/0040791 A1 | 2/2003 | Oktay |
| 2003/0065386 A1 | 4/2003 | Weadock |
| 2003/0093145 A1 | 5/2003 | Lawrence-Brown et al. |
| 2003/0125796 A1 | 7/2003 | Dong |
| 2003/0130720 A1 | 7/2003 | DePalma et al. |
| 2003/0153968 A1 | 8/2003 | Geis et al. |
| 2003/0191523 A1 | 10/2003 | Hojeibane |
| 2003/0199967 A1 | 10/2003 | Hartley et al. |
| 2003/0204243 A1* | 10/2003 | Shiu .......................... 623/1.16 |
| 2003/0212449 A1 | 11/2003 | Cox |
| 2003/0236567 A1 | 12/2003 | Elliot |
| 2004/0015227 A1 | 1/2004 | Vardi et al. |
| 2004/0015229 A1 | 1/2004 | Fulkerson |
| 2004/0098091 A1 | 5/2004 | Erbel et al. |
| 2004/0106972 A1 | 6/2004 | Deaton |
| 2004/0106978 A1 | 6/2004 | Greenberg et al. |
| 2004/0133266 A1 | 7/2004 | Clerc et al. |
| 2004/0162606 A1 | 8/2004 | Thompson |
| 2004/0171978 A1 | 9/2004 | Shalaby |
| 2004/0181149 A1 | 9/2004 | Langlotz et al. |
| 2004/0215327 A1 | 10/2004 | Doig et al. |
| 2005/0033406 A1 | 2/2005 | Barnhart et al. |
| 2005/0049678 A1 | 3/2005 | Cocks et al. |
| 2005/0065545 A1 | 3/2005 | Wallace |
| 2005/0085900 A1 | 4/2005 | Case et al. |
| 2005/0102018 A1 | 5/2005 | Carpenter et al. |
| 2005/0102021 A1 | 5/2005 | Osborne |
| 2005/0131517 A1 | 6/2005 | Hartley et al. |
| 2005/0137682 A1* | 6/2005 | Justino .......................... 623/1.24 |
| 2005/0149166 A1 | 7/2005 | Schaeffer et al. |
| 2005/0154448 A1 | 7/2005 | Cully et al. |
| 2005/0171598 A1 | 8/2005 | Schaeffer |
| 2005/0203606 A1 | 9/2005 | VanCamp |
| 2005/0222667 A1 | 10/2005 | Hunt |
| 2005/0222668 A1 | 10/2005 | Schaeffer et al. |
| 2005/0222669 A1 | 10/2005 | Purdy |
| 2005/0266042 A1 | 12/2005 | Tseng |
| 2006/0015170 A1 | 1/2006 | Jones et al. |
| 2006/0052799 A1 | 3/2006 | Middleman et al. |
| 2006/0069426 A1 | 3/2006 | Weinberger |
| 2006/0100684 A1 | 5/2006 | Elliott |
| 2006/0149360 A1 | 7/2006 | Schwammenthal et al. |
| 2006/0155358 A1 | 7/2006 | LaDuca et al. |
| 2006/0155366 A1 | 7/2006 | LaDuca et al. |
| 2006/0167476 A1 | 7/2006 | Burdulis, Jr. et al. |
| 2006/0173530 A1 | 8/2006 | Das |
| 2006/0193892 A1 | 8/2006 | Furst et al. |
| 2006/0229709 A1 | 10/2006 | Morris et al. |
| 2006/0241740 A1 | 10/2006 | Vardi et al. |
| 2006/0271166 A1 | 11/2006 | Thill et al. |
| 2006/0276882 A1 | 12/2006 | Case et al. |
| 2006/0281966 A1 | 12/2006 | Peacock, III |
| 2007/0016281 A1 | 1/2007 | Melsheimer |
| 2007/0021822 A1 | 1/2007 | Boatman |
| 2007/0043425 A1 | 2/2007 | Hartley et al. |
| 2007/0050011 A1 | 3/2007 | Klein |
| 2007/0055326 A1 | 3/2007 | Farley et al. |
| 2007/0055350 A1 | 3/2007 | Erickson et al. |
| 2007/0055358 A1 | 3/2007 | Krolik et al. |
| 2007/0060989 A1 | 3/2007 | Deem et al. |
| 2007/0061002 A1 | 3/2007 | Paul, Jr. et al. |
| 2007/0073373 A1 | 3/2007 | Bonsignore |
| 2007/0088425 A1 | 4/2007 | Schaeffer |
| 2007/0112344 A1 | 5/2007 | Keilman |
| 2007/0135677 A1 | 6/2007 | Miller et al. |
| 2007/0142896 A1 | 6/2007 | Anderson et al. |
| 2007/0150051 A1 | 6/2007 | Arnault De La Menardiere et al. |
| 2007/0156167 A1 | 7/2007 | Connors et al. |
| 2007/0167898 A1 | 7/2007 | Peters et al. |
| 2007/0179598 A1 | 8/2007 | Duerig |
| 2007/0185565 A1 | 8/2007 | Schwammenthal et al. |
| 2007/0207186 A1 | 9/2007 | Scanlon et al. |
| 2007/0208410 A1 | 9/2007 | Berra et al. |
| 2007/0213805 A1 | 9/2007 | Schaeffer et al. |
| 2007/0213807 A1 | 9/2007 | Roubin |
| 2007/0219610 A1 | 9/2007 | Israel |
| 2007/0219627 A1 | 9/2007 | Chu |
| 2007/0233229 A1 | 10/2007 | Berra et al. |
| 2007/0237973 A1 | 10/2007 | Purdy et al. |
| 2007/0244542 A1 | 10/2007 | Greenan et al. |
| 2007/0244543 A1 | 10/2007 | Mitchell |
| 2007/0244547 A1 | 10/2007 | Greenan |
| 2007/0250154 A1 | 10/2007 | Greenberg |
| 2007/0255388 A1 | 11/2007 | Rudakov et al. |
| 2008/0002871 A1 | 1/2008 | Gunzert-Marx et al. |
| 2008/0015673 A1 | 1/2008 | Chuter |
| 2008/0058918 A1 | 3/2008 | Watson |
| 2008/0109066 A1 | 5/2008 | Quinn |
| 2008/0114444 A1 | 5/2008 | Yu |
| 2008/0114445 A1 | 5/2008 | Melsheimer et al. |
| 2008/0147173 A1 | 6/2008 | McIff et al. |
| 2008/0167704 A1 | 7/2008 | Wright et al. |
| 2008/0195191 A1 | 8/2008 | Luo |
| 2008/0262595 A1 | 10/2008 | Chu et al. |
| 2008/0269789 A1 | 10/2008 | Eli |
| 2008/0275540 A1 | 11/2008 | Wen |
| 2008/0275542 A1 | 11/2008 | LaDuca et al. |
| 2008/0288044 A1 | 11/2008 | Osborne |
| 2008/0294234 A1 | 11/2008 | Hartley et al. |
| 2008/0300665 A1 | 12/2008 | Lootz et al. |
| 2008/0319528 A1 | 12/2008 | Yribarren et al. |
| 2009/0012597 A1 | 1/2009 | Doig et al. |
| 2009/0012602 A1 | 1/2009 | Quadri |
| 2009/0030502 A1 | 1/2009 | Sun et al. |
| 2009/0048663 A1 | 2/2009 | Greenberg |
| 2009/0054967 A1 | 2/2009 | Das |
| 2009/0069882 A1 | 3/2009 | Venturelli |
| 2009/0082841 A1 | 3/2009 | Zacharias et al. |
| 2009/0099648 A1 | 4/2009 | Yu |
| 2009/0099649 A1 | 4/2009 | Chobotov et al. |
| 2009/0105809 A1 | 4/2009 | Lee et al. |
| 2009/0112233 A1 | 4/2009 | Xiao |
| 2009/0125096 A1 | 5/2009 | Chu et al. |
| 2009/0138067 A1 | 5/2009 | Pinchuk et al. |
| 2009/0149877 A1 | 6/2009 | Hanson et al. |
| 2009/0164001 A1 | 6/2009 | Biggs et al. |
| 2009/0227997 A1 | 9/2009 | Wang et al. |
| 2009/0240316 A1 | 9/2009 | Bruszewski |
| 2009/0248134 A1 | 10/2009 | Dierking et al. |
| 2009/0254170 A1 | 10/2009 | Hartley et al. |
| 2009/0259290 A1 | 10/2009 | Bruszewski et al. |
| 2009/0287145 A1 | 11/2009 | Cragg et al. |
| 2010/0004728 A1 | 1/2010 | Rao et al. |
| 2010/0029608 A1 | 2/2010 | Finley et al. |
| 2010/0063575 A1 | 3/2010 | Shalev |
| 2010/0161026 A1 | 6/2010 | Brocker et al. |
| 2010/0211159 A1 | 8/2010 | Schmid et al. |
| 2010/0256725 A1 | 10/2010 | Rasmussen |
| 2010/0292774 A1 | 11/2010 | Shalev |
| 2011/0093002 A1 | 4/2011 | Rucker et al. |
| 2011/0125251 A1 | 5/2011 | Cottone |
| 2011/0208296 A1 | 8/2011 | Duffy et al. |
| 2011/0208297 A1 | 8/2011 | Tuval et al. |
| 2011/0208298 A1 | 8/2011 | Tuval et al. |

(56) References Cited

U.S. PATENT DOCUMENTS

| | | |
|---|---|---|
| 2011/0218607 A1 | 9/2011 | Arbefeuille et al. |
| 2011/0264184 A1 | 10/2011 | Heltai |

FOREIGN PATENT DOCUMENTS

| | | |
|---|---|---|
| EP | 1 177 780 | 2/2002 |
| EP | 1 325 716 | 7/2003 |
| JP | 2002-253682 | 9/2002 |
| WO | 2004/017868 | 3/2004 |
| WO | 2005/002466 | 1/2005 |
| WO | 2005/037138 | 4/2005 |
| WO | 2005/041781 | 5/2005 |
| WO | 2005/041783 | 5/2005 |
| WO | 2006/007389 | 1/2006 |
| WO | 2006/028925 | 3/2006 |
| WO | 2006/028925 A1 | 3/2006 |
| WO | 2006/070372 | 7/2006 |
| WO | 2007/022495 | 2/2007 |
| WO | 2007/084547 | 7/2007 |
| WO | 2007/144782 | 12/2007 |
| WO | 2008/008291 | 1/2008 |
| WO | 2008/035337 | 3/2008 |
| WO | 2008/042266 | 4/2008 |
| WO | 2008/047092 | 4/2008 |
| WO | 2008/047354 | 4/2008 |
| WO | 2008/053469 | 5/2008 |
| WO | 2008/107885 | 9/2008 |
| WO | 2008/140796 | 11/2008 |
| WO | 2009/078010 | 6/2009 |
| WO | 2009/116041 | 9/2009 |
| WO | 2009/116042 | 9/2009 |
| WO | 2009/118733 | 10/2009 |
| WO | 2010/024869 | 3/2010 |
| WO | 2010/024879 | 3/2010 |
| WO | 2010/031060 | 3/2010 |
| WO | 2010/045238 | 4/2010 |
| WO | 2010/062355 | 6/2010 |
| WO | 2010/088776 | 8/2010 |
| WO | 2010/128162 | 11/2010 |
| WO | 2010/150208 | 12/2010 |
| WO | 2011/004374 | 1/2011 |
| WO | 2011/007354 | 1/2011 |
| WO | 2011/055364 | 5/2011 |
| WO | 2011/064782 | 6/2011 |
| WO | 2011/067764 | 6/2011 |
| WO | 2011/070576 | 6/2011 |
| WO | 2011/080738 | 7/2011 |
| WO | 2011/095979 | 8/2011 |
| WO | 2011/106532 | 9/2011 |
| WO | 2011/106533 | 9/2011 |
| WO | 2011/106544 | 9/2011 |

OTHER PUBLICATIONS

Fonseca A et al., "Intravascular ultrasound assessment of the novel AngioSculpt scoring balloon catheter for the treatment of complex coronary lesions," J Invasive Cardiol 20(1):21-7 (Jan. 2008).

Khlif H et al., "Contribution to the Improvement of Textile Vascular Prostheses Crimping," Trends in Applied Sciences Research 6(9):1019-1027 (2011).

An International Search Report dated Feb. 18, 2010, which issued during the prosecution of Applicant's PCT/IL08/000287.

A Written Opinion dated Nov. 12, 2009, which issued during the prosecution of Applicant's PCT/IL08/000287.

An International Search Report dated Apr. 28, 2011, which issued during the prosecution of Applicant's PCT/IB2010/052861.

A Written Opinion dated Dec. 23, 2011, which issued during the prosecution of Applicant's PCT/IB2010/052861.

An International Search Report dated Dec. 3, 2010, which issued during the prosecution of Applicant's PCT/IL2010/000564.

A Written Opinion dated Jan. 14, 2012, which issued during the prosecution of Applicant's PCT/IL2010/000564.

An International Search Report dated Nov. 5, 2010, which issued during the prosecution of Applicant's PCT/IL2010/000549.

An Office Action dated Apr. 27, 2011, which issued during the prosecution of U.S. Appl. No. 12/447,684.

A Written Opinion dated Jan. 9, 2012, which issued during the prosecution of Applicant's PCT/IL2010/000549.

An Office Action dated Nov. 12, 2010, which issued during the prosecution of U.S. Appl. No. 12/447,684.

An International Search Report dated Oct. 6, 2011, which issued during the prosecution of Applicant's PCT/IL2010/000999.

An International Search Report dated Mar. 10, 2011, which issued during the prosecution of Applicant's PCT/IL2010/000917.

An International Search Report dated Jun. 9, 2011, which issued during the prosecution of Applicant's PCT/IL2010/001018.

An International Search Report dated Jun. 16, 2011, which issued during the prosecution of Applicant's PCT/IL2010/001037.

An International Search Report dated Jul. 7, 2011, which issued during the prosecution of Applicant's PCT/IL2010/001087.

An International Search Report dated Aug. 11, 2011, which issued during the prosecution of Applicant's PCT/IL2011/000135.

An International Search Report dated Mar. 11, 2010, which issued during the prosecution of Applicant's PCT/IL2008/001621.

A Written Opinion dated Jun. 15, 2010, which issued during the prosecution of Applicant's PCT/IL2008/001621.

An International Search Report dated Sep. 3, 2009, which issued during the prosecution of Applicant's PCT/IL2007/001312.

A Written Opinion dated Jul. 31, 2009, which issued during the prosecution of Applicant's PCT/IL2007/001312.

An English translation of an Office Action dated Aug. 25, 2011, which issued during the prosecution of Chinese Patent Application No. 200880014919.9.

Fattori et al., Degenerative aneurysm of the descending aorta. Endovascular Treatment. pp. 1-11, 2007, European Association for Cardio-Thoracic Surgery.

Van Prehn J et al., "Oversizing of aortic stent grafts for abdominal aneurysm repair: a systematic review of the benefits and risks," Eur J Vasc Endovasc Surg. Jul. 2009;38(1):42-53. Epub May 9, 2009 (abstract only).

An Office Action dated Jun. 19, 2012, which issued during the prosecution of U.S. Appl. No. 12/808,037.

An Office Action issued in Canadian Application No. 2,767,596, dated Nov. 3, 2014.

An Office Action issued in Chinese Application No. 201080036970.7, dated Oct. 8, 2014.

An International Search Report and a Written Opinion both dated Oct. 4, 2012, which issued during the prosecution of Applicant's PCT/IL2012/000269.

An International Search Report and a Written Opinion both dated Aug. 31, 2012, which issued during the prosecution of Applicant's PCT/IL2012/000148.

An International Search Report and a Written Opinion both dated Sep. 6, 2012, which issued during the prosecution of Applicant's PCT/IL2012/000190.

An International Search Report and a Written Opinion both dated Sep. 24, 2012, which issued during the prosecution of Applicant's PCT/IL2012/00060.

An International Search Report and a Written Opinion both dated Oct. 1, 2012, which issued during the prosecution of Applicant's PCT/IL2012/000241.

An Office Action dated Oct. 11, 2012, which issued during the prosecution of U.S. Appl. No. 13/031,871.

An International Search Report and a Written Opinion both dated Mar. 15, 2013, which issued during the prosecution of Applicant's PCT/IL2012/050424.

An Office Action dated May 20, 2013, which issued during the prosecution of U.S. Appl. No. 13/807,880.

International Search Report and Written Opinion for corresponding International Patent Application mailed Nov. 5, 2010.

Search Report (PCT/ISA/220, PCT/ISA/210 & PCT/ISA/237) dated Nov. 26, 2013, issued by the International Searching Authority in corresponding Application No. PCT/IL13/50656.

* cited by examiner

APPARATUS FOR CLOSURE OF A LUMEN AND METHODS OF USING THE SAME

CROSS-REFERENCE TO RELATED APPLICATIONS

The present patent application is the U.S. national stage of International Application PCT/IL2010/000549, filed Jul. 8, 2010, which claims priority from US Provisional Patent Application 61/224,089, filed Jul. 9, 2009, entitled, "Apparatus for closure of a lumen and methods of using the same," which is incorporated herein by reference.

FIELD OF THE APPLICATION

The present invention relates generally to minimally-invasive surgical apparatus and methods, and specifically to minimally-invasive apparatus and techniques for puncture site management.

BACKGROUND OF THE APPLICATION

Many vascular procedures are performed using minimally invasive techniques, often by accessing the femoral artery or another major blood vessel through a puncture opening made in the blood vessel, and accessing a surgical site via the blood vessel. Upon completion of the procedure, the puncture opening must be closed. The goal of repair of the puncture opening is to create hemostasis in tissue of the tissue tract leading to the blood vessel wall, and to allow the puncture opening to seal. Sealing the puncture opening allows blood to eventually flow again through the blood vessel without thrombosis or embolism, and allows the tissue in the tissue tract leading to the vessel to heal.

The earliest technique for closing a puncture opening was the simple application of direct physical pressure, either by a medical professional, and/or by a simple clamp. A drawback of direct pressure is that is it often painful for the patient, and requires extended immobilization of the patient and attention of the medical professional.

As an alternative to direct pressure, various devices for wound closure at a vascular puncture site have been developed, including biodegradable plugs, sutures, staples, ultrasound, collagen, collagen with thrombin, collagen with an anchor, and hemostatic patches and pads. Typically, these devices and technique are generally effective for closing punctures having that are suitable for delivery of up to 16 French endovascular systems.

Commercial alternatives to direct pressure include:
Angio-Seal™ Vascular Closure Device (St. Jude Medical, Inc., St. Paul, Minn.)
Perclose™ (Abbott Laboratories, Abbott Park, Ill.)
VasoSeal™ (Datascope, Montvale, N.J.)
Duett™ (Vascular Solutions, Minneapolis, Minn.)
HeartStitch® (Sutura, Fountain Valley, Calif.)
Syvek® hemostasis products (Marine Polymer Technologies, Inc., Danvers, Mass.)

U.S. Pat. No. 6,743,195 to Zucker describes apparatus for hemostasis of an artery having a puncture after arterial catheterization. The apparatus includes a catheter introducer having a forward end, and a hemostasis device including an elongate flexible hollow shaft having an inflatable anchor balloon at a forward end thereof, and an inflatable peripheral balloon adjacent the forward end of the flexible hollow shaft. The hemostasis device is arranged to be insertable into an artery via the catheter introducer.

U.S. Pat. No. 7,731,732 to Ken describes a closure device for closing a puncture wound having a distal section that can be placed against the interior wall of a vessel, and a proximal section that bunches in the tissue tract to close the wound. One variation of the device provides for removing the distal section from the vessel so that it resides also in the tissue tract after the proximal section has been securely bunched and lodged within the tissue tract in order to provide unobstructed fluid flow in the vessel.

The following patents may be of interest:
U.S. Pat. No. 5,527,322 to Klein et al.
U.S. Pat. No. 5,613,974 to Andreas et al.
U.S. Pat. No. 5,728,134 to Barak
U.S. Pat. No. 5,860,991 to Klein et al.
U.S. Pat. No. 5,921,994 to Andreas et al.
U.S. Pat. No. 6,117,145 to Wood et al.
U.S. Pat. No. 6,206,893 to Klein et al.
U.S. Pat. No. 6,846,321 to Zucker
U.S. Pat. No. 7,008,441 to Zucker
U.S. Pat. No. 7,115,127 to Lindenbaum et al.
U.S. Pat. No. 7,223,266 to Lindenbaum et al.
U.S. Pat. No. 7,662,168 to McGuckin, Jr. et al.
U.S. Pat. No. 7,662,161 to Briganti et al.
US Patent Application Publication 2006/0167476 to Burdulis, Jr. et al.

SUMMARY OF APPLICATIONS

In some applications of the present invention, a generally tubular endovascular prosthesis provides hemostasis to a puncture site in a body lumen, such as of blood vessel. The prosthesis comprises structural stent elements, and includes first and second structural portions, which meet each other at a juncture. The prosthesis is initially folded at the juncture, such that second structural portion is folded within the first structural portion. The prosthesis is introduced into the lumen via the puncture while in this folded state, and positioned several centimeters from the puncture site. The prosthesis is unfolded in the lumen, such that a portion of the second structural portion extends alongside the puncture site, thereby at least partially covering and blocking blood flow to the puncture site. For some applications, the prosthesis further comprises a blood-impervious fluid flow guide, which at least partially covers the second structural portion.

The structural stent elements of the second structural portion provide at least partial tissue scaffolding to enable hemostasis at the puncture site, and provide a surface that stimulates blood coagulation. The stent elements also reduce blood flow in the vicinity of the puncture site, enabling quicker healing of the puncture site. The first structural portion helps hold the entire prosthesis in place by providing good contact with the lumen wall. The first structural portion also may impede blood penetration into the space between the second structural portion and the puncture site.

The curative features of the prosthesis described in the preceding paragraph are provided by the prosthesis even in configurations that do not include the fluid flow guide, particularly if the structural stent elements have a high density, realized, for example, by a tight braided structure. In configurations that include the fluid flow guide, the fluid flow guide also helps seal the puncture site, and stimulates tissue growth and coagulation.

There is therefore provided, in accordance with an application of the present invention, apparatus including a generally tubular endovascular prosthesis, which is configured to transition between a radially-compressed state and a radially-expanded state, the prosthesis including:

a first structural portion, which has first and second ends, and which is generally cylindrical when the prosthesis assumes the radially-expanded state; and a second structural portion, which has first and second ends, and which is generally cylindrical when the prosthesis assumes the radially-expanded state, wherein the first end of the first structural portion and the first end of the second structural portion meet each other at a juncture, and wherein the prosthesis is configured to transition from (a) an initial folded state, in which the second structural portion is folded into the first structural portion at the juncture, such that the second end of the second structural portion axially extends in a direction from the juncture toward the second end of the first structural portion, to (b) an unfolded state, in which the second structural portion is no longer positioned within the first structural portion, and the second end of the first structural portion and the second end of the second structural portion are positioned at opposite ends of the prosthesis.

For some applications, the prosthesis further includes a blood-impervious fluid flow guide, which at least partially covers the second structural portion. Optionally, the fluid flow guide is biodegradable, in which case the biodegradable polymer may be selected from the group consisting of starch, gelatin, dextran, dextrin, alginate, hydroxypropyl methylcellulose, hydroxypropyl cellulose, polyvinyl alcohol, poly(L-lactic acid), poly(lactide-co-glycolide), polyethylene glycol, polycaprolactone, polyphosphate ester, poly(hydroxy-butyrate), poly(glycolic acid), poly(DL-lactic acid), poly(amino acid), chitosan, collagen and cellulose, polyethylenecarbonate, and a mixture thereof.

For some applications, the second structural portion is shaped so as to define an elongated opening that extends axially along at least a portion of the second structural portion, when the prosthesis assumes the radially-expanded state. For some applications, an arc of the second structural portion circumscribed by the elongated opening is generally constant along an entire length of the elongated opening. Alternatively, an arc of the second structural portion circumscribed by the elongated opening may be less at a first end of the elongated opening than at a second end of the elongated opening, which second end of the elongated opening is closer to the second end of the second structural portion than the first end of the elongated opening is to the second end of the second structural portion. Optionally, the arc may monotonically increase from the first end of the elongated opening to the second end of the elongated opening.

For some applications, the first end of the first structural portion is shaped so as to define a plurality of first loops, the first end of the second structural portion is shaped so as to define a plurality of second loops, and the first loops are interconnected with the second loops so as to define the juncture.

For some applications, an average diameter of the first structural portion is greater than an average diameter of the second structural portion, when the prosthesis assumes the radially-expanded and unfolded states. For some applications, a diameter of a portion of the first structural portion increases toward the second end thereof. For some applications, a diameter of a portion of the second structural portion increases toward the second end thereof.

For some applications, the first structural portion is flared radially outward at the first end thereof, when the prosthesis assumes the radially-expanded and unfolded states. Alternatively or additionally, the second structural portion may be flared radially outward at the second end thereof, when the prosthesis assumes the radially-expanded and unfolded states.

For any of the applications described above, the apparatus may further include a first elongated member, which is initially in contact with the first structural portion, and the first elongated member and the prosthesis are arranged such that axial motion of the first elongated member with respect to the prosthesis results in radial expansion of the first structural portion. For some applications, the first elongated member includes a first generally tubular sheath, which is initially externally positioned surrounding at least a portion of the first structural portion, such that the first sheath initially holds the prosthesis in the radially-compressed state. Optionally, the first sheath may be slidable with respect to the first structural portion.

For some applications, the apparatus further includes a second elongated member, which is initially in contact with the second structural portion, and the second elongated member and the prosthesis are arranged such that axial motion of the second elongated member with respect to the prosthesis transitions the prosthesis to the unfolded state. For some applications, the second elongated member and the prosthesis are arranged such that the axial motion of the second elongated member with respect to the prosthesis transitions the prosthesis to the unfolded state and results in radial expansion of the second structural portion. For some applications, the second elongated member is initially positioned between the second structural portion and a central longitudinal axis of the prosthesis. For some applications, the second elongated member and the second structural portion are configured such that the second elongated member is frictionally adherent to the second structural portion. For some applications, the second elongated member includes a second generally tubular sheath, which is shaped so as to define an internal lumen sized to allow passage therethrough of a guidewire.

For any of the applications mentioned above, the apparatus may further include sterile packaging, in which the prosthesis is initially stored in the radially-compressed and initial folded states.

For any of the applications mentioned above, the first and second structural portions may include a plurality of structural stent elements. For some applications, the structural stent elements include a super-elastic alloy. For some applications, the prosthesis is configured to be self-expandable. For some applications, the super-elastic alloy includes Nitinol. For some applications, the super-elastic alloy includes a material selected from the group consisting of: a braided super-elastic alloy, and a woven super-elastic alloy.

There is further provided, in accordance with an application of the present invention, a method for providing hemostasis to a puncture site in a body lumen, the method including:

providing a generally tubular endovascular prosthesis, which includes first and second structural portions that meet each other at a juncture;

introducing the prosthesis into the lumen via the puncture site, while the prosthesis is in a radially-compressed state and an in an initial folded state, in which the second structural portion is folded into the first structural portion at the juncture; and while the prosthesis is within the lumen, transitioning the prosthesis (a) from the radially-compressed state to a radially-expanded state, and (b) from the initial folded state to an unfolded state, in which unfolded state the second structural portion is no longer positioned within the first structural portion, such that a portion of the second portion extends alongside the puncture site.

For some applications, providing the prosthesis includes providing the prosthesis in which:

the first structural portion has first and second ends, and is generally cylindrical when the prosthesis assumes the radially-expanded state, the second structural portion has first and second ends, and is generally cylindrical when the prosthesis assumes the radially-expanded state, the second end of the second structural portion axially extends in a direction from the juncture toward the second end of the first structural portion, when the prosthesis assumes the initial folded state, and the second end of the first structural portion and the second end of the second structural portion are positioned at opposite ends of the prosthesis, when the prosthesis assumes the unfolded state.

For some applications, providing the prosthesis includes providing the prosthesis in which the first end of the first structural portion is shaped so as to define a plurality of first loops, the first end of the second structural portion is shaped so as to define a plurality of second loops, and the first loops are interconnected with the second loops so as to define the juncture.

For some applications, transitioning the prosthesis from the radially-compressed state to a radially-expanded state includes radially expanding the first structural portion by axially moving a first elongated member that is initially in contact with the first structural portion. For some applications, the first elongated member includes a first generally tubular sheath, which is initially externally positioned surrounding at least a portion of the first structural portion, such that the first sheath initially holds the prosthesis in the radially-compressed state, and radially expanding the first structural portion includes removing the first sheath from the at least a portion of the first structural portion. For some applications, removing includes sliding the first sheath with respect to the first structural portion.

For some applications, transitioning the prosthesis from the initial folded state to the unfolded state includes axially moving a second elongated member that is initially in contact with the second structural portion. For some applications, transitioning the prosthesis from the radially-compressed state to the radially-expanded state includes radially expanding the second structural portion by axially moving the second elongated member. For some applications, providing the prosthesis includes providing the prosthesis such that the second elongated member is initially positioned between the second structural portion and a central longitudinal axis of the prosthesis. For some applications, the second elongated member includes a second generally tubular sheath, which is shaped so as to define an internal lumen, and introducing the prosthesis includes advancing a guidewire into lumen via the puncture site, and advancing the prosthesis over the guidewire that passes through the lumen.

For some applications, providing the prosthesis includes providing the prosthesis including a blood-impervious fluid flow guide, which at least partially covers the second structural portion.

For some applications, providing the prosthesis includes providing the prosthesis in which the second structural portion is shaped so as to define an elongated opening that extends axially along at least a portion of the second structural portion, when the prosthesis assumes the radially-expanded state.

For some applications, providing the prosthesis includes providing the prosthesis in which the first and second structural portions include structural stent elements. For some applications, providing the prosthesis includes providing the prosthesis in which the structural stent elements include a super-elastic alloy. For some applications, providing the prosthesis includes providing the prosthesis configured to be self-expandable. For some applications, providing the prosthesis includes providing the prosthesis in which the super-elastic alloy includes a material selected from the group consisting of: a braided super-elastic alloy, and a woven super-elastic alloy.

For some applications, introducing the prosthesis includes positioning the prosthesis such that the juncture is at a distance from the puncture site of between 0.5 and 3 cm. Alternatively or additionally, introducing the prosthesis may include positioning the prosthesis such that the juncture is at a distance from the puncture site of between 0.1 and 1.5 times a diameter of the lumen at the puncture site.

The present invention will be more fully understood from the following detailed description of embodiments thereof, taken together with the drawings, in which:

DETAILED DESCRIPTION OF APPLICATIONS

Figure 1:
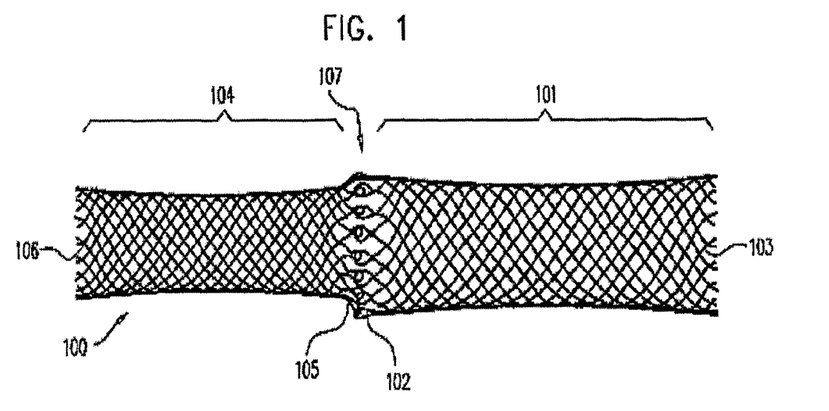
FIGS. 1-3 are schematic illustrations of a generally tubular endovascular prosthesis, in accordance with respective applications of the present invention.
Figure 2:
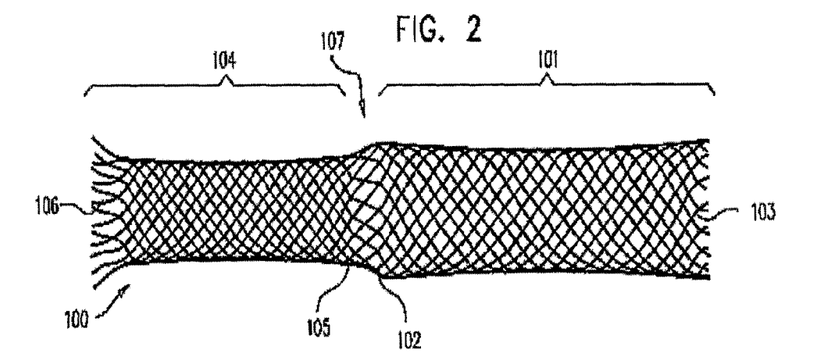
Figure 3:
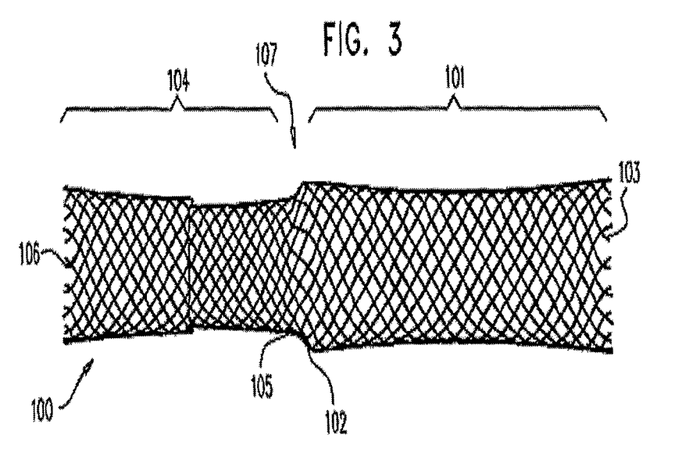

FIGS. 1-3 are schematic illustrations of a generally tubular endovascular prosthesis 100, in accordance with respective applications of the present invention. Prosthesis 100 is configured to transition from a radially-compressed state, as described hereinbelow with reference to FIGS. 7B and 8A, to a radially-expanded state, as shown in FIGS. 1-3 and some of the other figures. Prosthesis 100 is also configured to transition between an initial folded state, as described hereinbelow with reference to FIGS. 4, 5, and 7C-D, to a subsequent unfolded state, as shown in FIGS. 1-3 and some of the other figures.

Prosthesis 100 comprises a first structural portion 101, which has first and second ends 102 and 103, and a second structural portion 104, which has first and second ends 105 and 106. Each of the first and second structural portions is generally cylindrical when the prosthesis assumes the radially-expanded and unfolded states. In the unfolded state shown in FIG. 1-3, second structural portion 104 is no longer positioned within first structural portion 101, and second end 103 of first structural portion 101 and second end 106 of second structural portion 104 are positioned at opposite ends of prosthesis 100.

The first and second structural portions comprise a plurality of structural stent elements, which typically comprise a metal, such as a super-elastic alloy, e.g., Nitinol. For some applications, the prosthesis is relaxed in the radially-expanded state. For some applications, the prosthesis is configured to be self-expandable. For some applications, the structural stent elements are braided or woven, such as for applications in which the structural stent elements comprise the super-elastic alloy.

First end 102 of first structural portion 101 and first end 105 of second structural portion 104 meet each other at a juncture 107 axially between first structural portion 101 and second structural portion 104 when the prosthesis assumes the unfolded state. For some applications, as shown in FIG. 1, first end 102 of first structural portion 101 is shaped so as to define a plurality of first loops, and first end 105 of second structural portion 104 is shaped so as to define a plurality of second loops. The first loops are interconnected with the second loops so as to define juncture 107. For other applications, as shown in FIG. 2, first and second structural portions 101 and 104 are integral elements of prosthesis 100. For these applications, joint 107 is optionally defined by structural stent elements that are configured to facilitate folding, e.g., the structural stent elements may be extended in comparison to other stent elements of the prosthesis.

For some applications, a length of first structural portion 101 is at least 1 cm, no more than 10 cm, and/or between 1 and 10 cm, such as between 2 and 5 cm, when prosthesis 100 assumes the radially-expanded and unfolded states. For some applications, a length of second structural portion 104 is at least 0.5 cm, no more than 6 cm, and/or between 0.5 and 6 cm, such as between 1 and 4 cm, when prosthesis 100 assumes the radially-expanded and unfolded states. For some applications, when prosthesis 160 assumes the radially-expanded and unfolded states, first structural portion 101 is longer than second structural portion 104, such as at least 20% longer, no more than 100% longer, and/or between 20% and 100% longer, such as between 30% and 80% longer. For other applications, first and second structural portions 101 and 104 are of equal length, or second structural portion 104 is longer than first structural portion 101. In the latter case, second end 106 of second structural portion 104 may protrude distally beyond second end 103 of first structural portion 101 when the prosthesis assumes the initial folded state (configuration not shown).

For some applications, a length of prosthesis 100 is at least 1.5 cm, no more than 16 cm, and/or between 1.5 and 16 cm, such as between 3 and 9 cm, when prosthesis 100 assumes the radially-expanded and unfolded states. For some applications, a length of prosthesis 100 is at least 2 cm, no more than 20 cm, and/or between 2 and 20 cm, such as between 3 and 10 cm, when prosthesis 100 assumes the radially-compressed and folded states.

For some applications, a diameter of first structural portion 101 is generally constant along its length, as shown in FIG. 1, when prosthesis 100 assumes the radially-expanded and unfolded states. For example, an outer diameter of first structural portion 101 may be at least 3 mm, no more than 20 mm, and/or between 3 and 20 mm, such as between 4 and 15 mm. For some applications, a diameter of second structural portion 104 is generally constant along its length, as shown in FIG. 1. For example, an outer diameter of second structural portion 104 may be at least 2.5 mm, no more than 20, and/or between 2.5 and 20 mm, such as between 4 and 12 mm.

For some applications, an average diameter of first structural portion 101 is greater than an average diameter of second structural portion 104, such as between 10% and 40% greater. The smaller diameter of the second structural portion may increase the ease of unfolding the second structural portion from within the first structural portion, as described hereinbelow with reference to FIGS. 7E-7G and 8B-C. The larger diameter of the first structural portion may provide better alignment of the prosthesis with the wall of the lumen.

For other applications, the diameters of the structural portions are equal, or the diameter of the second structural portion is greater than the diameter of the first structural portion. (When the prosthesis assumes the initial folded state, as described hereinbelow, even if the diameter of the second structural portion is greater than the diameter of the first structural portion, the second structural portion can typically fit within the first structural portion. For example, for applications in which the structural stent elements are braided, the second structural portion axially expands when radially compressed.)

For some applications, as shown in FIG. 2, first structural portion 101 is flared radially outward at second end 103, and/or second structural portion 104 is flared radially outward at second end 106. The main bodies (i.e., the non-flared portions) of the structural portions may have the diameters and relative diameters described in the preceding paragraphs. The flare at second end 106 may help prevent blood from entering the space between second structural portion 104 and the lumen wall, even in configurations in which prosthesis 100 does not comprise fluid flow guide 108, as described hereinbelow with reference to FIG. 5. (For applications in which second structural portion 104 is implanted downstream from first structural portion 104, some blood generally flows upstream during diastole.)

For some applications, one or more of the flares may be provided in combination with the looped junction described hereinabove with reference to FIG. 1, or the increasing diameters described hereinbelow with reference to FIG. 3.

For still other applications, as shown in FIG. 3, the diameter of a portion of first structural portion 101 (typically near second end 103) increases (such as monotonically increases) toward second end 103, and/or the diameter of a portion of second structural portion 104 (typically near second end 106) increases (such as monotonically increases) toward second end 106. A portion of the increase in the diameter of second structural portion 104 is optionally provided by a step, as shown in FIG. 3.

Figure 4:
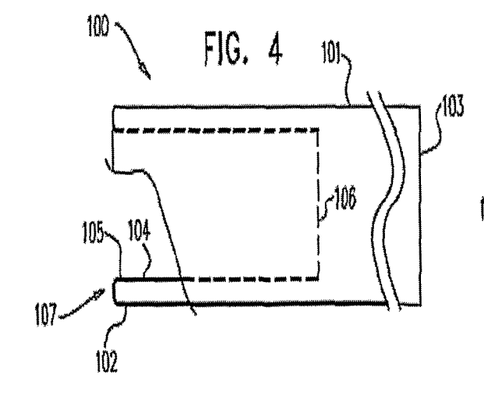
FIGS. 4 and 5 are schematic cross-sectional and perspective illustrations, respectively, of the prosthesis of FIGS. 1-3 in an initial folded state, in accordance with an application of the present invention.
Figure 5:
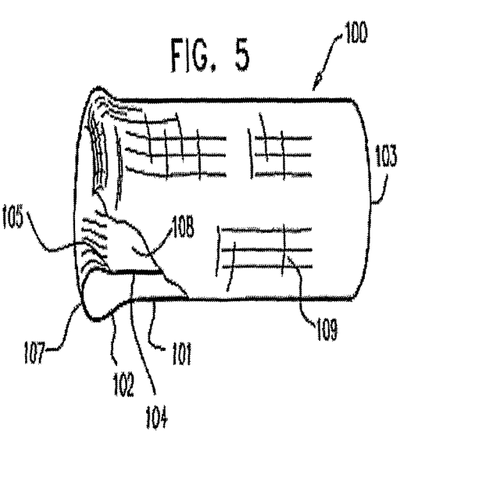

Reference is now made to FIGS. 4 and 5, which are schematic cross-sectional and perspective illustrations, respectively, of prosthesis 100 in the initial folded state, in accordance with an application of the present invention. In the initial folded sate, second structural portion 104 is folded into first structural portion 101 at juncture 107, such that second end 106 of second structural portion 104 axially extends in a direction from juncture 107 toward second end 103 of first structural portion 101 (the direction is rightward in FIGS. 4 and 5). Second end 106 may or may not extend all of the way to second end 103, and optionally extends beyond second end 103.

It is noted that FIGS. 4 and 5 show second structural portion 104 folded within first structural portion 101 while the second structural portion is radially expanded. For some applications, as described hereinbelow with reference to FIGS. 7C-F and 8A-B, the second structural portion is at least partially (e.g., entirely) radially compressed while folded within the first structural portion.

For some applications, as shown in FIG. 5, prosthesis 100 further comprises a blood-impervious fluid flow guide 108, which at least partially covers second structural portion 104. Alternatively or additionally, for some applications, prosthesis 100 further comprises a blood-impervious fluid flow guide 109, which at least partially covers first structural portion 101. For some applications, one or both of the fluid flow guides is biodegradable. For example, one or both of the fluid flow guides may comprise a biodegradable polymer, which may, for example, be selected from the group consisting of: starch, gelatin, dextran, dextrin, alginate, hydroxypropyl methylcellulose, hydroxypropyl cellulose, polyvinyl alcohol, poly(L-lactic acid), poly(lactide-co-glycolide), polyethylene glycol, polycaprolactone, polyphosphate ester, poly(hydroxy-butyrate), poly(glycolic acid), poly(DL-lactic acid), poly(amino acid), chitosan, collagen and cellulose, polyethylenecarbonate, and a mixture thereof.

Figure 6A:
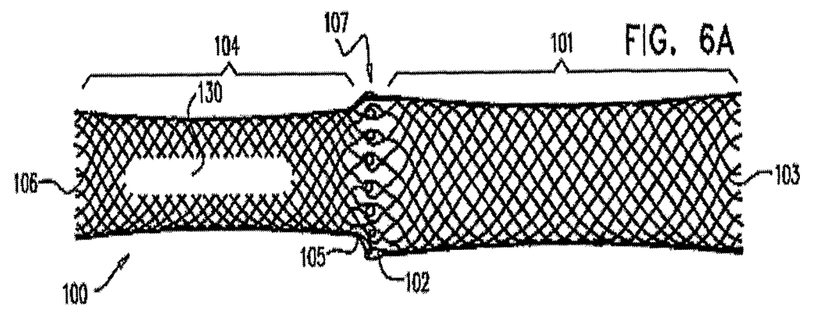
FIGS. 6A-C are schematic illustration of a configuration of the prosthesis of FIGS. 1-3 having an elongated opening, in accordance with an application of the present invention.
Figure 6B:
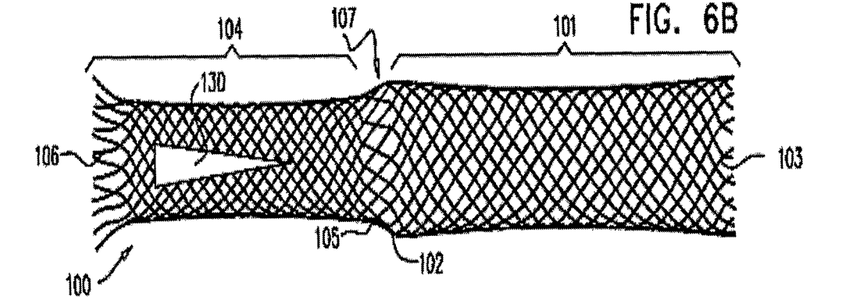
Figure 6C:
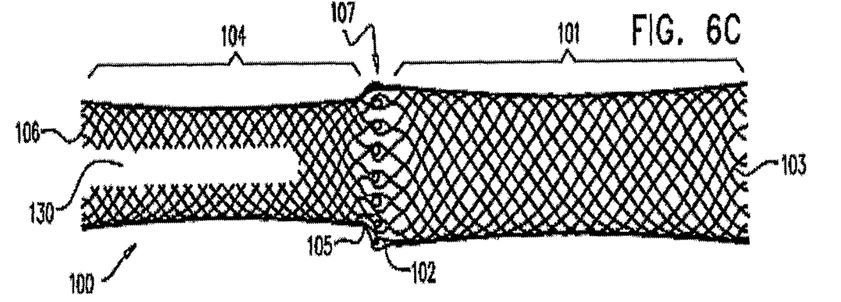

Reference is made to FIGS. 6A-C, which are schematic illustrations of configurations of prosthesis 100 having an elongated opening 130, in accordance with respective applications of the present invention. In these configurations, second structural portion 104 is shaped so as to define at least one elongated opening 130 (i.e., a circumferential discontinuation in the structural stent elements of portion 104) that extends axially along at least a portion of the second structural portion, when the prosthesis assumes the radially-expanded state. For example, the at least one elongated opening may comprise exactly one elongated opening, or two, three, four, or more elongated openings. The at least one elongated opening reduces the radial compressive strength of second structural portion 104, thereby enabling the second structural portion to be more readily folded into and unfolded out of the first structural portion. Elongated opening 130 may be implemented in combination with any of the other features of prosthesis 100 described herein, including, but not limited to, fluid flow guide 108.

For some applications, elongated opening 130 extends along only a portion of second structural portion 104, as shown in FIGS. 6A-C, while for other applications, the elongated opening extends along the entire length of portion 104 (configuration not shown). For some applications, elongated opening 130 extends to second end 106 of the portion 104, as shown in FIG. 6C. For some applications, a length of elongated opening 130 is at least 2 mm, no more than 30 mm, and/or between 2 and 30 mm, such as between 4 and 20 mm. For some applications, a length of elongated opening 130 is at least 20%, no more than 80%, and/or between 20% and 80% of a length of second structural portion 104, such as between 30% and 50%.

For some applications, as shown in FIGS. 6A and 6C, an arc of the prosthesis circumscribed by the elongated opening is generally constant along an entire length of the elongated opening, such that a width of elongated opening is generally constant. For other applications, as shown in FIG. 6B, the arc of the prosthesis circumscribed by the elongated opening is less at a first end of the elongated opening than at a second end of the elongated opening, which second end of the elongated opening is closer to second end 106 of second structural portion 104 than the first end of the elongated opening is to second end 106. Alternatively, for some applications, the arc is greater at the first end of the elongated opening than at the second end of the elongated opening (configuration not shown). For some applications, the arc increases (such as monotonically increases) from the first end of the elongated opening to the second end of the elongated opening, as shown in FIG. 6B, or from the second end of the elongated opening to the first end of the elongated opening (configuration not shown). For example, the elongated opening may be generally triangular, as shown in FIG. 6B. For some applications, the arc of prosthesis circumscribed by elongated opening 130 (or by each of elongated openings 130, if more than one are provided) is at least 20 degrees, no more than 50 degrees, and/or between 20 and 30 degrees.

During implantation of the prosthesis, as described hereinbelow with reference to FIGS. 7A-G and 8A-C, it is important that elongated opening 130 does not overlap with the puncture site. In order to enable the surgeon to properly rotationally orient the prosthesis to prevent such overlap, the elongated opening(s) and/or another site on the prosthesis may be provided with one or more markers indicating the location(s) of the elongated opening(s).

For some applications, opening 130 is not elongated, and instead has another shapes, such as circular or square. Optionally, for these applications, second elongated member 114, described hereinbelow with reference to FIGS. 7B and 8A, passes through opening 130, rather than through second end 106 of second structural portion 104.

Reference is now made to FIGS. 7A-G, which are schematic illustrations of a method for introducing and deploying prosthesis 100 through a puncture site 111 into a body lumen 110, in accordance with an application of the present invention. FIGS. 8A-C are schematic cross-sectional illustrations of a portion of the steps of the method, in accordance with an application of the present invention. Body lumen 110 may be a blood vessel, such as an artery (e.g., the iliac artery, the femoral artery, the radial artery, or the brachiocephalic artery), or a corresponding vein (e.g., the iliac vein, the femoral vein, the radial vein, the brachiocephalic vein, or the chiocephalic vein, or the esophageous, or other segments of the gastro-intestinal tract, such as the small intestine or large intestine.

Figure 7A:
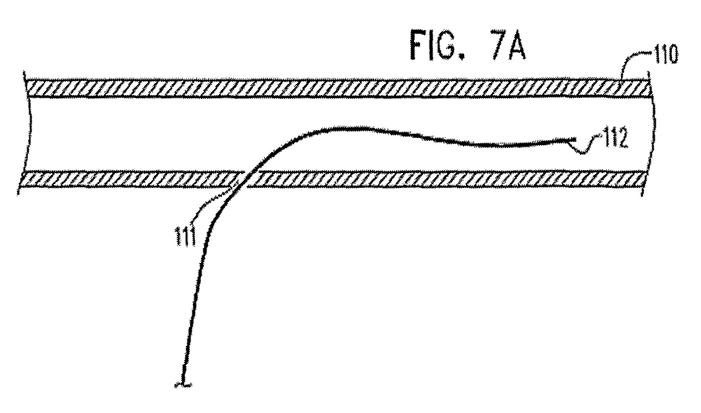
FIGS. 7A-G are schematic illustrations of a method for introducing and deploying the prosthesis of FIGS. 1-3 through a puncture site into a body lumen, in accordance with an application of the present invention.
Figure 8A:
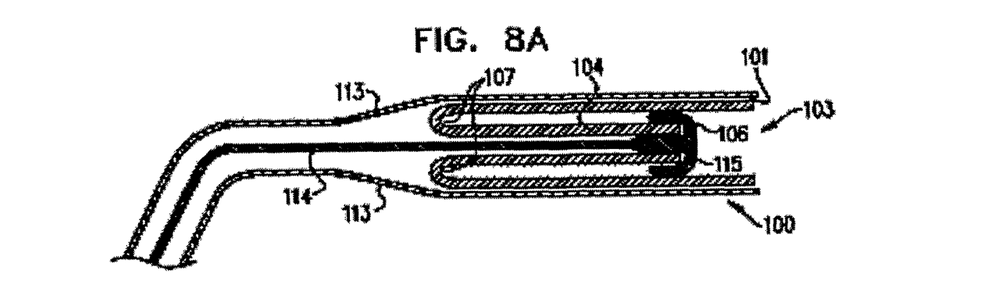
FIGS. 8A-C are schematic cross-sectional illustrations of a portion of the steps of the method of FIGS. 7A-G, in accordance with an application of the present invention.
Figure 8B:
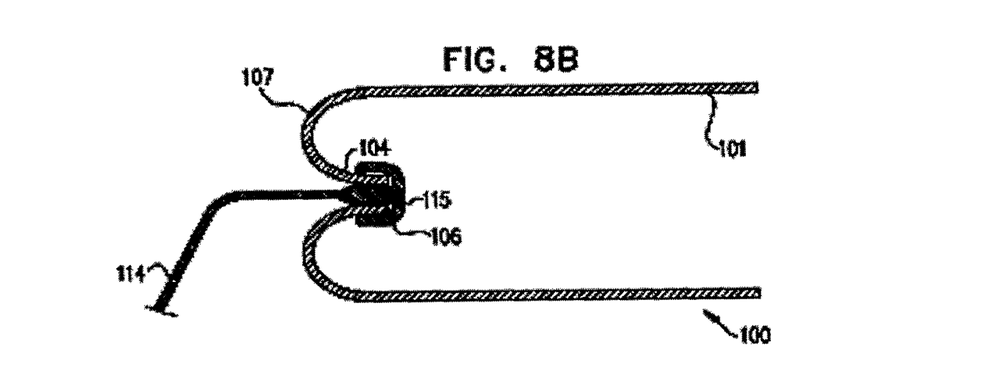
Figure 8C:
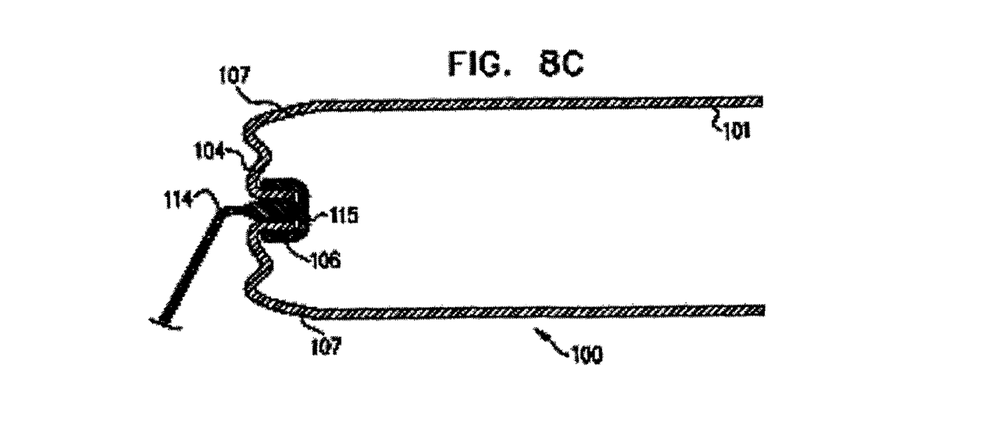

As shown in FIG. 7A, the procedure begins with the insertion of a guidewire 112 through puncture site 111 into body lumen 110. The puncture was typically previously made during a transvascular procedure, to enable insertion of a treatment or diagnostic device into body lumen 110 (and optionally into another body lumen, compartment, or organ thereafter). Prosthesis 100 can generally be used for closing punctures that are suitable for delivery of catheters that are essentially unlimited in their outer diameter. Typically, the prosthesis is initially stored in sterile packaging in the radially-compressed and initial folded states. All or a portion of the elements used to introduce and deploy the prosthesis, such as described hereinbelow, may also be stored in the same sterile packaging, or in separate sterile packaging.

Figure 7B:
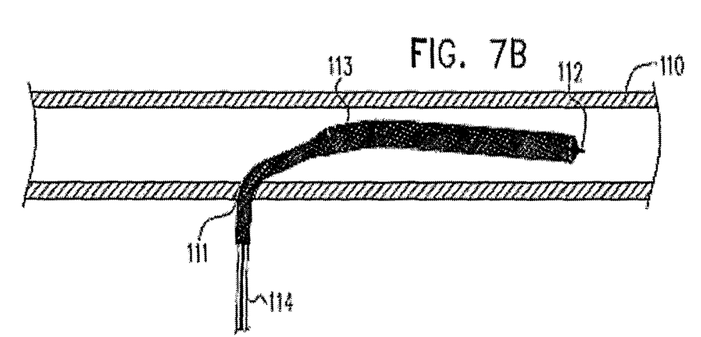

As shown in FIGS. 7B and 8A, prosthesis 100 is introduced over guidewire 112 in the radially-compressed and initial folded states. The prosthesis is typically positioned such that juncture 107 (which is located at the proximal end of the prosthesis when the prosthesis is in the initial folded state) is between about 0.5 and 3 cm distally from puncture site 111, such as between 0.5 and 2 cm, and/or at a distance from the puncture site of between 0.1 and 1.5 times a diameter of the lumen at the puncture site. Typically, the prosthesis is oriented such that juncture 107 is between puncture site 111 and second end 103 of first structural portion 101. For some applications, the prosthesis is introduced and deployed using a deployment tool, which comprises a first elongated member 113, which is initially in contact with first structural portion 101, and/or a second elongated member 114, which is initially in contact with second structural portion 104. First elongated member 113 and prosthesis 100 are arranged such that axial motion of first elongated member 113 with respect to prosthesis 100 results in radial expansion of first structural portion 101. For example, such axial motion may be caused by proximally pulling the first elongated member toward the surgeon. Second elongated member 114 and prosthesis 100 are arranged such that axial motion of second elongated member 114 with respect to prosthesis 100 transitions the prosthesis to the unfolded state. For example, such axial motion may be caused by proximally pulling the second elongated member toward the surgeon. For some applications, for example as described in more detail below, second elongated member 114 and prosthesis 100 are arranged such that the axial motion of the second elongated member with respect to the prosthesis transitions the prosthesis to the unfolded state and results in radial expansion of the second structural portion.

Figure 7C:
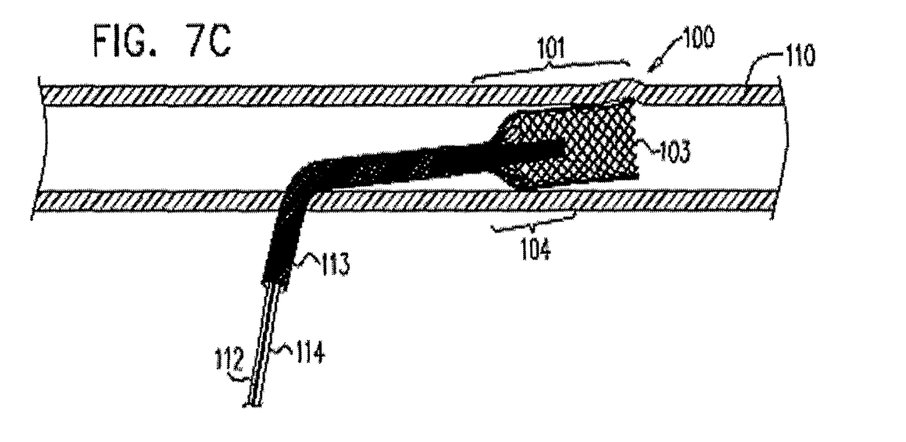

For some applications, first shaft member 113 comprises a first generally tubular sheath, as shown in FIGS. 7B, 7C, and 8A. The first sheath is initially externally positioned surrounding at least a portion of first structural portion 101, such as the entire first structural portion. The first sheath initially holds prosthesis 100 in the radially-compressed state.

Figure 7D:
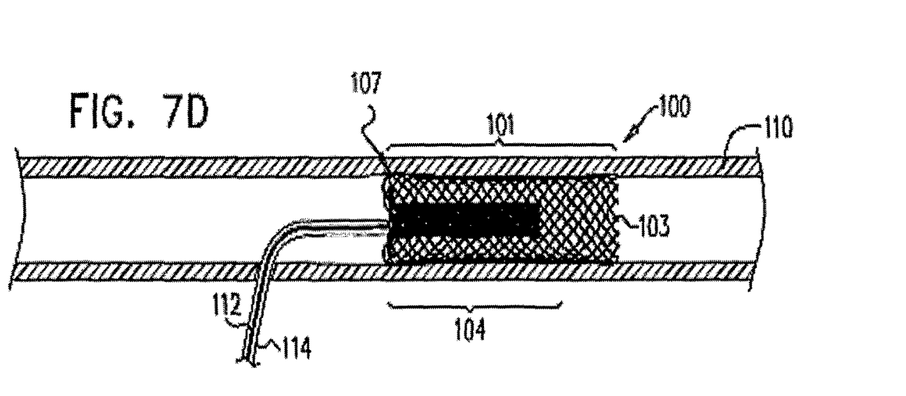

As shown in FIGS. 7C, 7D, and 8B, the first sheath is withdrawn proximally from the prosthesis, allowing first structural portion 101 to expand radially outward. To enable this withdrawal of the first sheath, the first sheath is slidable with respect to the first structural portion; optionally, the first sheath may be internally lubricated. For some applications, as shown in the figures, second structural portion 104 remains at least partially radially compressed toward a central longitudinal axis of the prosthesis. Alternatively, the second structural portion expands radially outward at this stage of deployment (configuration not shown).

Figure 7E:
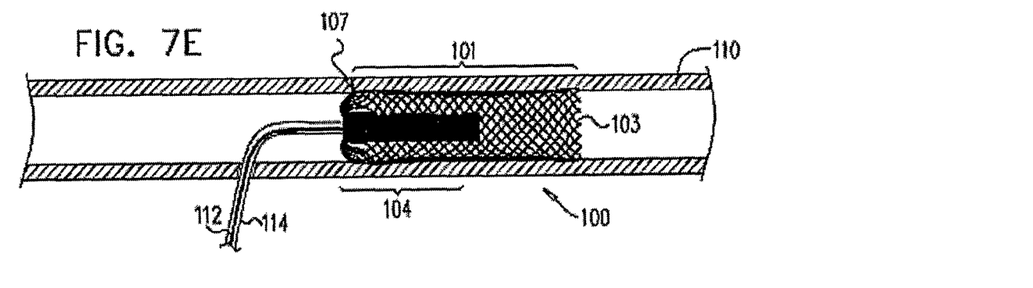
Figure 7F:
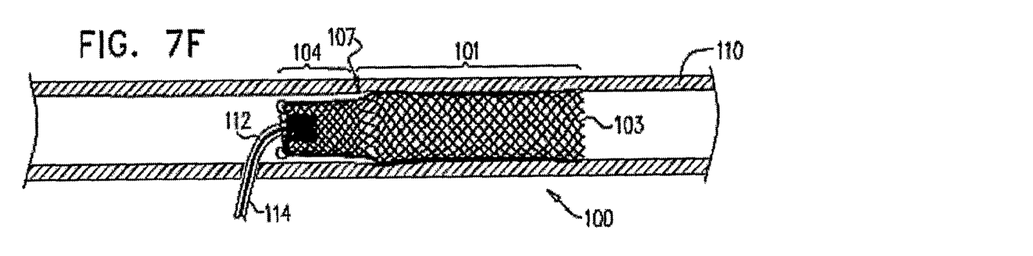

For some applications, as shown in FIGS. 7D-F, and most clearly in FIGS. 8A-C, second elongated member 114 is initially positioned within the second structural portion. In other words, the second elongated member is positioned between the second structural portion and a central longitudinal axis of the prosthesis. Withdrawing the second elongated member in a proximal direction, as shown in FIGS. 7E-F and 8B-C, causes second structural portion 104 to unfold from within first structural portion 101. For some applications, the second elongated member and the second structural portion are configured such that the second elongated member is frictionally adherent to the second structural portion. As a result, the second elongated member pulls the second structural portion proximally as the second elongated member is withdrawn proximally. Alternatively or additionally, second elongated member 114 is shaped so as to define or comprises an engagement element 115 at a distal end of the second elongated member, as shown in FIGS. 8A-C. The engagement element is configured to removably engage second end 106 of second structural portion 104, and to pull second 106 proximally as second elongated member 114 is withdrawn proximally. For some applications, the second elongated member comprises silicone, a high-friction elastomer, or a fluoropolymer, such as PTFE, PET, or PEEK.

For some applications, the second elongated member comprises a second generally tubular sheath, which may comprise, for example, silicone, polyurethane, fluoropolymer, or another material. Typically, the second sheath is shaped so as to define an internal lumen sized to allow passage therethrough of guidewire 112. (For clarity of illustration, guidewire 112 is not shown in FIGS. 8A-C, although it is typically provided.)

Alternatively, for some applications, first elongated member 113 comprises a shaft, and/or second elongated member 114 comprises a shaft (configuration not shown). Alternatively or additionally, second elongated member 114 is removably coupled to second end 106 of second structural portion 104. For some applications, elongated member 113 comprises an engagement element that is removably coupled to second end 103 of first structural portion 101 (configuration not shown). The engagement element initially holds the prosthesis in the radially-compressed state. Upon removal of the engagement element, the prosthesis transitions to the radially-expanded state.

Figure 7G:
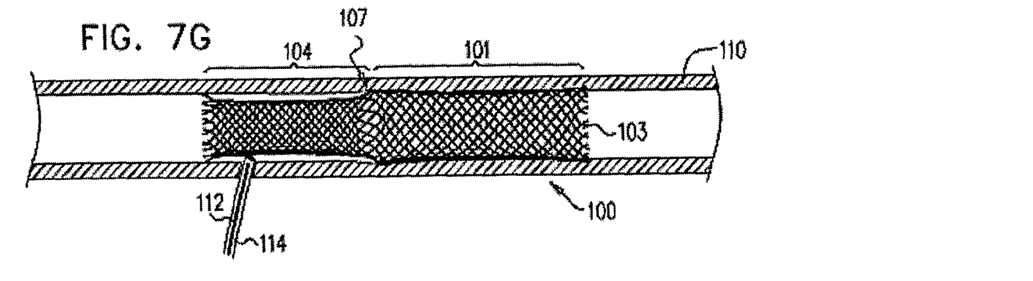

Upon complete proximal withdrawal of second elongated member 114 from second structural portion 104, prosthesis 100 completes the transition to the unfolded state, as shown in FIG. 7G. A portion of second structural portion 104 extends alongside puncture site 111 in body lumen 110, thereby at least partially covering and blocking blood flow to the puncture site. The prosthesis is typically left permanently in place in the lumen. For some applications, all or a portion of the structural stent elements is biodegradable (for example, stent crowns may be biostable, while connective members that connect the stent crowns may be biodegradable, such that flexibility of the blood vessel is maintained in the long term and future percutaneous procedures are facilitated.

The structural stent elements of second structural portion 104 provide at least partial tissue scaffolding to enable hemostasis, and provide a surface that stimulates blood coagulation. The stent elements also reduce blood flow in the vicinity of puncture site 111, enabling quicker healing of the puncture site. First structural portion 101 helps hold the entire prosthesis in place by providing good contact with the lumen wall. The first structural portion also may impede blood penetration into the space between the second structural portion and the puncture site.

The curative features of prosthesis 100 described in the preceding paragraph are provided by prosthesis 100 even in configurations that do not include fluid flow guide 108, described hereinabove with reference to FIG. 5, particularly if the structural stent elements have a high density, realized, for example, by a tight braided structure. In configurations that include fluid flow guide 108, the fluid flow guide also helps seal the puncture site, and stimulates tissue growth and coagulation.

Prosthesis 100 is typically a stand-alone device, which is not integrated or coupled to any other implantable treatment or diagnostic devices. Alternatively, for some applications, prosthesis 100 may be coupled to or integral with another implantable treatment or diagnostic device, such as a stent component of another device, e.g., an endovascular stent-graft, such as for treating an aortic aneurysm.

As used in the present application, including the claims, "proximal" means toward puncture site 111 (and the surgeon), and "distal" means away from the puncture site (and the surgeon). For applications in which the body lumen is a blood vessel, distal may be either upstream or downstream, depending on the direction in which the prosthesis is advanced into the blood vessel after passing through the puncture site.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising a generally tubular endovascular prosthesis, which comprises structural stent elements, and which is configured to transition between a radially-compressed state and a radially-expanded state, the prosthesis comprising:

a first structural portion, (a) which comprises a plurality of the structural stent elements, (b) which has first and second ends, and (c) which is generally cylindrical when the prosthesis assumes the radially-expanded state; and a second structural portion, (a) which comprises a plurality of the structural stent elements, (b) which has first and second ends, and (c) which is generally cylindrical when the prosthesis assumes the radially-expanded state, wherein the first end of the first structural portion and the first end of the second structural portion meet each other at a juncture, and wherein the prosthesis is configured to transition from (a) an initial folded state, in which the second structural portion is folded into the first structural portion at the juncture, such that the second end of the second structural portion axially extends in a direction from the juncture toward the second end of the first structural portion, to (b) an unfolded state, in which the second structural portion is no longer positioned within the first structural portion, and the second end of the first structural portion and the second end of the second structural portion are positioned at opposite ends of the prosthesis.

2. The apparatus according to claim 1, wherein the prosthesis further comprises a blood-impervious fluid flow guide, which at least partially covers the second structural portion.

3. The apparatus according to claim 2, wherein the fluid flow guide is biodegradable.

4. The apparatus according to claim 1, wherein the second structural portion is shaped so as to define an elongated opening that extends axially along at least a portion of the second structural portion, when the prosthesis assumes the radially-expanded state.

5. The apparatus according to claim 4, wherein an arc of the second structural portion circumscribed by the elongated opening is less at a first end of the elongated opening than at a second end of the elongated opening, which second end of the elongated opening is closer to the second end of the second structural portion than the first end of the elongated opening is to the second end of the second structural portion.

6. The apparatus according to claim 5, wherein the arc monotonically increases from the first end of the elongated opening to the second end of the elongated opening.

7. The apparatus according to claim 1, wherein the first end of the first structural portion is shaped so as to define a plurality of first loops, wherein the first end of the second structural portion is shaped so as to define a plurality of second loops, and wherein the first loops are interconnected with the second loops so as to define the juncture.

8. The apparatus according to claim 1, wherein the second structural portion is flared radially outward at the second end thereof, when the prosthesis assumes the radially-expanded and unfolded states.

9. The apparatus according to claim 1, further comprising a first elongated member, which is initially in contact with the first structural portion, wherein the first elongated member and the prosthesis are arranged such that axial motion of the first elongated member with respect to the prosthesis results in radial expansion of the first structural portion.

10. The apparatus according to claim 9, wherein the first elongated member comprises a first generally tubular sheath, which is initially externally positioned surrounding at least a portion of the first structural portion, such that the first sheath initially holds the prosthesis in the radially-compressed state, and wherein the first sheath is slidable with respect to the first structural portion.

11. The apparatus according to claim 9, further comprising a second elongated member, which is initially in contact with the second structural portion, wherein the second elongated member and the prosthesis are arranged such that axial motion of the second elongated member with respect to the prosthesis transitions the prosthesis to the unfolded state.

12. The apparatus according to claim 11, wherein the second elongated member and the prosthesis are arranged such that the axial motion of the second elongated member with respect to the prosthesis transitions the prosthesis to the unfolded state and results in radial expansion of the second structural portion.

13. The apparatus according to claim 11, wherein the second elongated member is initially positioned between the second structural portion and a central longitudinal axis of the prosthesis, and wherein the second elongated member and the second structural portion are configured such that the second elongated member is frictionally adherent to the second structural portion.

14. The apparatus according to claim 1, wherein the structural stent elements comprise a super-elastic alloy.

15. The apparatus according to claim 14, wherein the super-elastic alloy comprises a material selected from the group consisting of: a braided super-elastic alloy, and a woven super-elastic alloy.

16. The apparatus according to claim 1, wherein the prosthesis does not comprise a blood-impervious fluid flow guide that at least partially covers the second structural portion.

17. A method for providing hemostasis to a puncture site in a body lumen, the method comprising:

providing a generally tubular endovascular prosthesis, which (1) includes structural stent elements, (2) is configured to transition between a radially-compressed state and a radially-expanded state, and (3) includes (i) a first structural portion, (a) which includes a plurality of the structural stent elements, (b) which has first and second ends, and (c) which is generally cylindrical when the prosthesis assumes the radially-expanded state, and (ii) a second structural portion, (a) which comprises a plurality of the structural stent elements, (b) which has first and second ends, and (c) which is generally cylindrical when the prosthesis assumes the radially-expanded state, wherein the first end of the first structural portion and the first end of the second structural portion meet each other at a juncture;

introducing the prosthesis into the lumen via the puncture site, while the prosthesis is in the radially-compressed state and an in an initial folded state, in which the second structural portion is folded into the first structural portion at the juncture, such that the second end of the second structural portion axially extends in a direction from the juncture toward the second end of the first structural portion; and while the prosthesis is within the lumen, transitioning the prosthesis (a) from the radially-compressed state to the radially-expanded state, and (b) from the initial folded state to an unfolded state, in which unfolded state the second structural portion is no longer positioned within the first structural portion, and the second end of the first structural portion and the second end of the second structural portion are positioned at opposite ends of the prosthesis, such that a portion of the second portion extends alongside the puncture site.

18. The method according to claim 17, wherein providing the prosthesis comprises providing the prosthesis in which the first end of the first structural portion is shaped so as to define a plurality of first loops, the first end of the second structural portion is shaped so as to define a plurality of second loops, and the first loops are interconnected with the second loops so as to define the juncture.

19. The method according to claim 17, wherein transitioning the prosthesis from the radially-compressed state to a radially-expanded state comprises radially expanding the first structural portion by axially moving a first elongated member that is initially in contact with the first structural portion.

20. The method according to claim 19, wherein the first elongated member includes a first generally tubular sheath, which is initially externally positioned surrounding at least a portion of the first structural portion, such that the first sheath initially holds the prosthesis in the radially-compressed state, and wherein radially expanding the first structural portion comprises removing the first sheath from the at least a portion of the first structural portion.

21. The method according to claim 20, wherein removing comprises sliding the first sheath with respect to the first structural portion.

22. The method according to claim 19, wherein transitioning the prosthesis from the initial folded state to the unfolded state comprises axially moving a second elongated member that is initially in contact with the second structural portion.

23. The method according to claim 22, wherein transitioning the prosthesis from the radially-compressed state to the radially-expanded state comprises radially expanding the second structural portion by axially moving the second elongated member.

24. The method according to claim 22, wherein providing the prosthesis comprises providing the prosthesis such that the second elongated member is initially positioned between the second structural portion and a central longitudinal axis of the prosthesis.

25. The method according to claim 17, wherein providing the prosthesis comprises providing the prosthesis including a blood-impervious fluid flow guide, which at least partially covers the second structural portion.

26. The method according to claim 17, wherein providing the prosthesis comprises providing the prosthesis in which the second structural portion is shaped so as to define an elongated opening that extends axially along at least a portion of the second structural portion, when the prosthesis assumes the radially-expanded state.

27. The method according to claim 17, wherein providing the prosthesis comprises providing the prosthesis in which the structural stent elements comprise a super-elastic alloy.

28. The method according to claim 27, wherein providing the prosthesis comprises providing the prosthesis in which the super-elastic alloy includes a material selected from the group consisting of: a braided super-elastic alloy, and a woven super-elastic alloy.

29. The method according to claim 17, wherein introducing the prosthesis comprises positioning the prosthesis such that the juncture is at a distance from the puncture site of between 0.5 and 3 cm.

30. The method according to claim 17, wherein the prosthesis does not include a blood-impervious fluid flow guide that at least partially covers the second structural portion, and wherein providing the prosthesis comprises providing the prosthesis that does not include a blood-impervious fluid flow guide that at least partially covers the second structural portion.

31. The method according to claim 17, wherein transitioning comprises transitioning the prosthesis to the unfolded state such that the portion of the second portion extends alongside the puncture site, and the structural stent elements of the second portion provide at least partial tissue scaffolding to enable the hemostasis at the puncture site, and to provide a surface that stimulates blood coagulation.

* * * * *